United States Patent
Choudhary et al.

(10) Patent No.: US 11,866,690 B2
(45) Date of Patent: Jan. 9, 2024

(54) UPGRADING AND ENRICHMENT OF GASES THROUGH ALGAE PHOTOBIOREACTORS

(71) Applicant: ExxonMobil Technology and Engineering Company, Annandale, NJ (US)

(72) Inventors: Vinit Choudhary, Cypress, TX (US); Everett J. O'Neal, Asbury, NJ (US); Sarah E. Feicht, Raritan, NJ (US); Patrick L. Hanks, Bridgewater, NJ (US); Samantha J. Reuter, Houston, TX (US); Rachel G. Munson, Spring, TX (US)

(73) Assignee: ExxonMobil Technology and Engineering Company, Annandale, NJ (US)

( * ) Notice: Subject to any disclaimer, the term of this patent is extended or adjusted under 35 U.S.C. 154(b) by 358 days.

(21) Appl. No.: 17/019,392

(22) Filed: Sep. 14, 2020

(65) Prior Publication Data

US 2021/0079338 A1  Mar. 18, 2021

Related U.S. Application Data

(60) Provisional application No. 62/899,836, filed on Sep. 13, 2019.

(51) Int. Cl.
   C12N 1/12 (2006.01)
   C12M 1/00 (2006.01)

(52) U.S. Cl.
   CPC .............. *C12N 1/12* (2013.01); *C12M 21/02* (2013.01)

(58) Field of Classification Search
   None
   See application file for complete search history.

(56) References Cited

U.S. PATENT DOCUMENTS

| | | | |
|---|---|---|---|
| 8,415,142 B2 * | 4/2013 | Kertz | A01G 7/02 435/296.1 |
| 2013/0236951 A1 * | 9/2013 | Tseng | C12M 47/18 435/292.1 |

FOREIGN PATENT DOCUMENTS

EP   878533 A2 * 11/1998 ............ C12M 21/02

OTHER PUBLICATIONS

EngMT—Baezold, D. et al. Process and apparatus for the photobiological separation of carbon dioxide and methane containing gases. EP 0878533 A2; Date Published: Nov. 18, 1998; pp. 1-8; specif. pp. 1, 2, 3, 4, 5, 7.*

Morales, M. et al. 2018. The impact of environmental factors on carbon dioxide fixation by microalgae. FEMS Microbiology Letters 365: 1-11; specif. pp. 1, 5, 7.*

Datta, A.K. et al. 2006. Optimization of membrane unit for removing carbon dioxide from natural gas. Journal of Membrane Science 283: 291-300; specif. p. 291.*

Posten, C. 2009. Design principles of photo-bioreactors for cultivation of microalgae. Engineering in Life Sciences 9(3): 165-177; specif. pp. 165, 168ng gases. EP 0878533 A2; Date Published: Nov. 18, 1998; pp. 1-8; specif. pp. 1, 2, 3, 4, 5, 7.*

Hickman, D.A. et al. 1993. Production of syngas by direct catalytic oxidation of methane. Science 259: 343-346; specif. pp. 343, 345.*

Netusil, M. et al. 2011. Comparison of three methods for natural gas dehydration. Journal of Natural Gas Chemistry 20: 471-476; specif. pp. 471, 475, 476.*

Elliott, D.C. et al. 2012. Chemical processing in high-pressure aqueous environments. 9. Process development for catalytic gasification of algae feedstocks. Industrial & Engineering Chemistry Research 51: 10768-10777; specif. pp. 10768, 10771.*

* cited by examiner

*Primary Examiner* — Michael Barker
*Assistant Examiner* — Sharon M. Papciak
(74) *Attorney, Agent, or Firm* — SHOOK, HARDY & BACON L.L.P.

(57) ABSTRACT

A method includes containing an algae media within a contactor, introducing a stream of natural gas comprising up to 80 wt % carbon dioxide ($CO_2$) into the contactor, contacting the natural gas on the algae media and thereby allowing the algae media to consume $CO_2$ from the natural gas, and discharging a stream of natural gas comprising 2 wt % or less $CO_2$ from the contactor.

18 Claims, 2 Drawing Sheets

UPGRADING AND ENRICHMENT OF GASES THROUGH ALGAE PHOTOBIOREACTORS

CROSS-REFERENCE TO RELATED APPLICATIONS

This application claims the benefit of priority from U.S. Provisional Application No. 62/899,836 filed Sep. 13, 2019, which is herein incorporated by reference in its entirety.

BACKGROUND OF THE INVENTION

Concerns about climate change, carbon dioxide ($CO_2$) emissions, and depleting mineral oil and gas resources have led to widespread interest in the production of biofuels from algae and microalgae. Algae biomass is generally grown in a water slurry contained in a photobioreactor (PBR) using photosynthetic algae strains. The most common types of PBRs used in algal cultivation are open raceway ponds and tubular-type enclosed or open reactors. As compared to other plant-based feedstocks, algae have higher $CO_2$ fixation efficiencies and growth rates, and growing algae can efficiently utilize wastewater and industrial gases (e.g., $CO_2$) as nutrient sources. The most developed method for extracting biofuels from microalgae is converting their stored lipids into renewable diesel and jet fuel.

Algae are classified as photoautotrophic organisms, or organisms that can survive, grow and reproduce with energy derived entirely from the sun through the process of photosynthesis. Photosynthesis is essentially a carbon recycling process through which inorganic $CO_2$ is combined with solar energy, other nutrients, and cellular biochemical processes to synthesize carbohydrates and other compounds critical to life. The $CO_2$ most often comes from atmospheric air, an exhaust stream from a combustion process, or $CO_2$ storage locations (e.g., tanks, geological formations, etc.). Algae production may be optimized and more cost-effective by finding and utilizing new $CO_2$-rich sources to feed algae production.

Moreover, during photosynthesis, algae harvest solar energy and $CO_2$ to split water atoms and thereby produce biomass feedstock, and in the process, the algae release oxygen ($O_2$) as a byproduct. In open PBRs, the $O_2$ is naturally discharged into the surrounding atmosphere, but in closed PBRs the $O_2$ must be periodically or continually vented since excessive $O_2$ can oxidize the algae and inhibit its growth. Oxygen is a necessary reaction product in many industries that commonly employ expensive air separation units or oxygen generators to obtain the $O_2$ necessary for the desired reactions. Such air separation systems and oxygen generators, however, are expensive and energy intensive. Algae production can become more efficient and cost-effective by harvesting the $O_2$ byproduct for use in various oxygen-requiring processes.

SUMMARY OF THE INVENTION

The present disclosure is related to biofuel production from algae and, more particularly, to using high carbon dioxide concentration gases to grow algae within a photobioreactor and the efficient use of oxygen byproduct.

In some embodiments, a method includes containing an algae media within a contactor, introducing a stream of natural gas comprising up to 80 wt % carbon dioxide ($CO_2$) into the contactor, and contacting the natural gas on the algae media and thereby allowing the algae media to consume $CO_2$ from the natural gas. A stream of natural gas comprising 2 wt % or less $CO_2$ may then be discharged from the contactor.

In one or more additional embodiments, another method includes introducing a stream of natural gas into an algae photobioreactor (PBR) containing an algae media, generating oxygen ($O_2$) with the algae media, and stripping at least a portion of the $O_2$ with the natural gas within the PBR. The method may further include discharging a stream of natural gas enriched with $O_2$ from the PBR, and using the stream of natural gas enriched with $O_2$ in an oxygen-requiring process.

In one or more additional embodiments, another method includes introducing a stream of a high-carbon dioxide ($CO_2$) concentration gas into a contactor containing an algae media, the high-$CO_2$ concentration gas comprising at one of natural gas having up to 80 wt % $CO_2$ and a biogas having about 20-40 wt % $CO_2$, contacting the high-$CO_2$ concentration gas on the algae media and thereby allowing the algae media to consume $CO_2$ from the high-$CO_2$ concentration gas, and discharging a stream of gas comprising 2 wt % or less $CO_2$ from the contactor.

BRIEF DESCRIPTION OF THE DRAWINGS

The following figures are included to illustrate certain aspects of the present disclosure, and should not be viewed as exclusive embodiments. The subject matter disclosed is capable of considerable modifications, alterations, combinations, and equivalents in form and function, without departing from the scope of this disclosure.

DETAILED DESCRIPTION OF THE INVENTION

Figure 1:
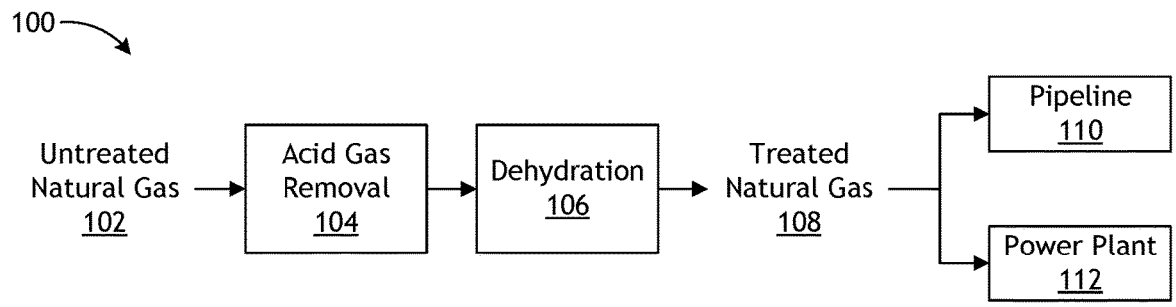
FIG. 1 is a schematic diagram of a prior art process of treating a raw, untreated natural gas stream.

Some embodiments of the present disclosure are directed to utilizing high carbon dioxide ($CO_2$) concentration gases for the growth and production of algae. Many natural gas reserves, for example, contain very high $CO_2$ content, which renders the development of such reserves economically less attractive. For example, a significant fraction of global natural gas reserves is challenged due to $CO_2$ content as high as 70-80 wt %, whereas typical natural gas pipeline specifications require $CO_2$ content at 2 wt % or less. In principle, natural gas with a high $CO_2$ content can be used for combustion in power generation, but it typically requires higher capital and operating expenses. The substantial cost of $CO_2$ removal and the inherent high $CO_2$ footprint of the process are big challenges in developing such natural gas reserves.

Another high-$CO_2$ concentration gas that is often overlooked is biogas generated from anaerobic digesters, which often has 20-40 wt % $CO_2$. The high $CO_2$ concentration in the biogas lowers its value and utilization potential for energy generation through combustion. If not removed from the biogas prior to combustion, the $CO_2$ is wasted to the atmosphere.

On the other hand, commercial-scale algae biofuel production commonly requires a continuous supply of $CO_2$ (e.g., several gigawatt power plant equivalent) for algae growth and it is often challenging to find large concentrated $CO_2$ sources. Embodiments disclosed herein propose a synergistic approach in which the $CO_2$ present in high-$CO_2$ concentration gases, such as natural gas or biogas streams, may be utilized for growing algae in algae photobioreactors (PBRs), which allows for the outlet capture of the gas with a reduced $CO_2$ concentration. This may enable efficient development of natural gas reserves and biogases derived from anaerobic digesters with high $CO_2$ content by providing a low cost $CO_2$ source for algae growth while simultaneously upgrading the quality of delivered gas.

Some embodiments of the present disclosure are further directed to efficiently utilizing the oxygen ($O_2$) byproduct generated during algae growth. Algae produces a substantial amount of $O_2$ as a byproduct of photosynthesis, and the generated $O_2$ constantly competes with $CO_2$ for some of the enzymes involved in the $CO_2$ fixation to generate biomass. Unless it is removed, the $O_2$ can inhibit algae growth and preclude efficient productivity of algae. Embodiments disclosed herein propose harvesting the $O_2$ generated by the algae media and using the captured $O_2$ in one or more oxygen-requiring processes that require oxygen as a reactant instead of being vented to the atmosphere. Example oxygen-requiring processes include, but are not limited to, syngas production, hydrogen production, and oxycombustion for power production.

Embodiments disclosed herein also propose enriching natural gas reserves or biogases with $O_2$ collected from an algae biofuel production PBR. More specifically, natural gas (methane) and biogases are commonly used for power generation and require $O_2$ for efficient combustion. The $O_2$ collected from an algae biofuel production may be combined with a natural gas or biogas stream to improve its combustion. In at least one embodiment, for instance, a natural gas or biogas stream may be introduced into the PBR to strip off the $O_2$ generated by the algae media and discharge a combustible gas enriched with $O_2$. Moreover, if the natural gas or biogas stream entering the PBR has a high $CO_2$ content, the algae media will consume the $CO_2$, thus simultaneously reducing the $CO_2$ content of the natural gas or biogas as it intermingles with the algae media.

FIG. 1 is a schematic diagram of a prior art process 100 of treating (preparing) a stream of raw, untreated natural gas 102. The natural gas 102 may be treated in the process 100 to meet pipeline or power plant combustion specifications, which often require certain limits on various chemical compositions. The untreated natural gas 102 may comprise any natural gas stream or reserve. The untreated natural gas 102, for example, may be derived from a subterranean hydrocarbon-bearing formation penetrated by any onshore or offshore producing wellbore. The untreated natural gas 102 may include, for example, amounts of methane ($CH_4$), $C_1$-$C_n$, $N_2$, $CO_2$, $H_2S$, and $H_2O$, and may further include trace amounts of other chemical compositions. In some cases, the untreated natural gas 102 may comprise up to about 80 wt % $CO_2$, but could be as low was 10 wt % or 5 wt %. As will be appreciated, the untreated natural gas 102 having high $CO_2$ concentration will oftentimes exceed pipeline specifications but can also exceed some power plant combustion specifications.

In the process 100, the untreated natural gas 102 may first be treated to remove acid gases, as at 104. When treating the natural gas 102 to meet pipeline specifications, the acid gas treatment 104 may be designed to remove chemical compositions, such as $H_2S$ and $CO_2$. During this process, the concentration of $CO_2$ in the stream of natural gas 102 may be reduced to about 2.0 wt %. When treating the natural gas 102 for power plant combustion specifications, however, the acid gas treatment 104 may be designed to remove only $H_2S$ while the concentration of the $CO_2$ can remain substantially unchanged.

The natural gas 102 may then be dehydrated, as at 106, to remove water ($H_2O$) from the stream and discharge a treated natural gas 108 having only trace amounts of $H_2S$ and $H_2O$. Depending on the specifics of the process 100, the treated natural gas 108 may then be conveyed to a pipeline 110 for transport to end users or to a power plant 112 for combustion.

Figure 2:
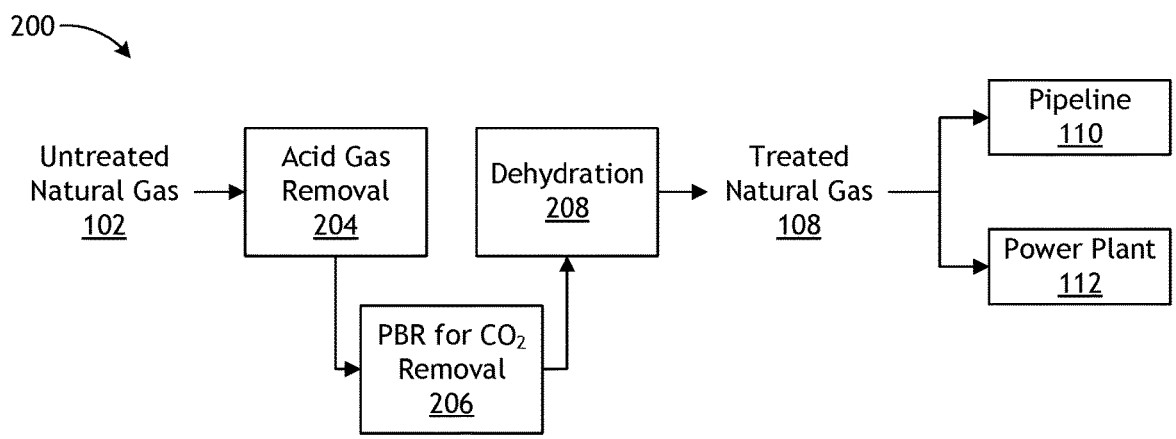
FIG. 2 is a schematic diagram of an example process of treating a raw, untreated natural gas stream, according to one or more embodiments of the disclosure.

FIG. 2 is a schematic diagram of an example process 200 of treating (preparing) the natural gas 102, according to one or more embodiments of the disclosure. Similar to the process 100 of FIG. 1, the untreated natural gas 102 in the process 200 may first be treated to remove acid gases, as at 204. Unlike the process 100, however, the acid gas treatment 204 may be designed to remove only $H_2S$ while the concentration of the $CO_2$ in the natural gas stream 102 may remain unchanged and up to about 80 wt %, as indicated above, but could be as low was 10 wt % or 5 wt %.

The stream of natural gas 102 may then be conveyed to an algae photobioreactor (PBR) to remove $CO_2$ from the natural gas 102, as at 206. More specifically, the natural gas 102 may be caused to interact with the algae media contained within the PBR and, in the process, the algae media will consume large concentrations of the $CO_2$ present in the natural gas 102. The PBR may comprise, for example, a tubular-type enclosed reactor. In some embodiments, as discussed below, some or all of the algae media from the PBR may be circulated to a contactor and the natural gas 102 may be introduced into the contactor to interact with the algae media. In other embodiments, the contactor may comprise the PBR. In some embodiments, after interacting with the algae media the natural gas 102 may have a $CO_2$ content of about 2 wt % or less.

After interacting with the algae contained within the PBR (or contactor), as at 206, the natural gas 102 may then be dehydrated, as at 208, to remove water ($H_2O$) from the stream and discharge the treated natural gas 108 having a $CO_2$ content of about 2 wt % or less, along with trace amounts of $H_2S$ and $H_2O$. The treated natural gas 108 may then be conveyed to a pipeline 110 for transport to end users or to a power plant 112 for combustion.

In some embodiments, the foregoing process 200 may alternatively be used to treat (prepare) any high-$CO_2$ concentration gas, such as a biogas derived from an anaerobic digester. Accordingly, in such embodiments, the natural gas 102 in the process 200 may be replaced with "biogas" and may be processed (treated) similarly. Anaerobic digesters convert organic materials to biogas typically containing 20-40 wt % $CO_2$ along with methane ($CH_4$). Similar to natural gas reserves having a high $CO_2$ concentration, a high concentration of $CO_2$ in biogas lowers its value and its combustion potential for energy generation. On the other hand, if not removed from the biogas prior to combustion, the $CO_2$ is wasted to the atmosphere.

Figure 3:
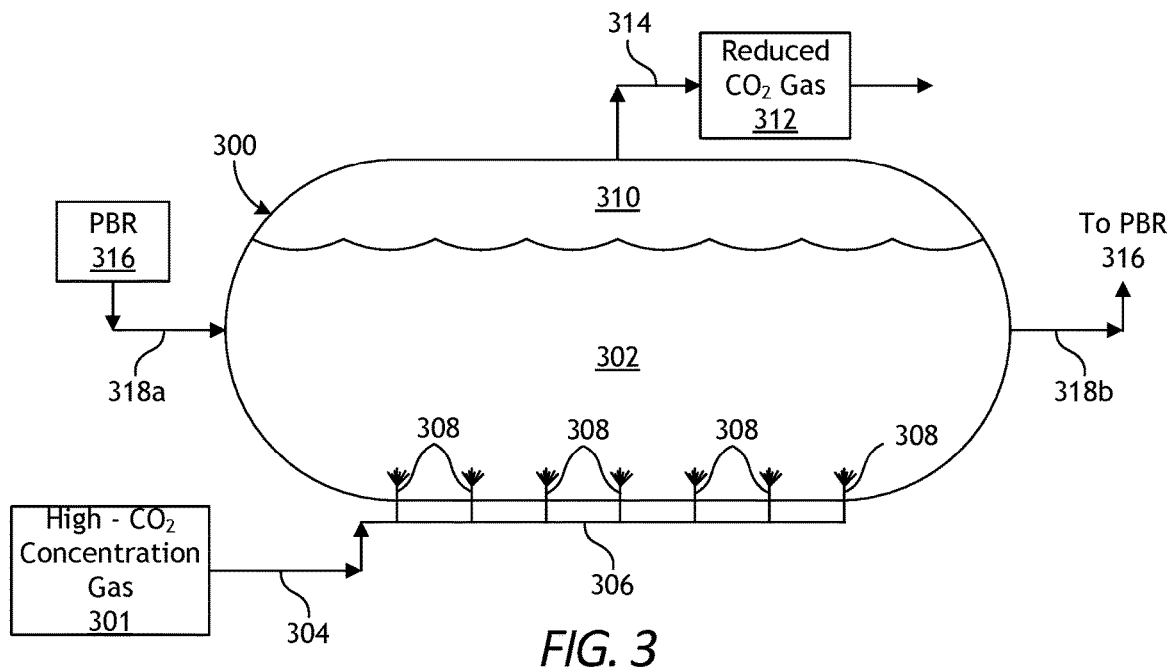
FIG. 3 is a schematic diagram of an example contactor that may be used to interact a natural gas stream with algae media, according to one or more embodiments.

FIG. 3 is a schematic diagram of an example contactor 300 that may be used to interact (contact) a high-$CO_2$ concentration gas 301 with algae media 302, according to one or more embodiments of the disclosure. In some embodiments, the high-$CO_2$ concentration gas 301 may comprise the stream of untreated, natural gas 102 described above, but may alternatively comprise a biogas derived from an anaerobic digester. The algae media 302 may comprise an aqueous culture of photosynthetic microorganisms, generally comprising water combined with an algae feedstock and maintained in conditions suitable for the growth and harvesting of algae for biofuel production.

Algal sources for the algae growing within the algae media 302 can include, but are not limited to, unicellular and multicellular algae. Examples of such algae can include a rhodophyte, chlorophyte, heterokontophyte, tribophyte, glaucophyte, chlorarachniophyte, euglenoid, haptophyte, cryptomonad, dinoflagellum, phytoplankton, and the like, and combinations thereof. In one embodiment, algae can be of the classes Chlorophyceae and/or Haptophyta. Specific species can include, but are not limited to, *Neochloris oleoabundans, Scenedesmus dimorphus, Euglena gracilis, Phaeodactylum tricornutum, Pleurochrysis carterae, Prymnesium parvum, Tetraselmis chui*, and *Chlamydomonas reinhardtii*. Additional or alternate algal sources can include one or more microalgae of the *Achnanthes, Amphiprora, Amphora, Ankistrodesmus, Asteromonas, Boekelovia, Borodinella, Botryococcus, Bracteococcus, Chaetoceros, Carteria, Chlamydomonas, Chlorococcum, Chlorogonium, Chlorella, Chroomonas, Chrysosphaera, Cricosphaera, Crypthecodinium, Cryptomonas, Cyclotella, Dunaliella, Ellipsoidon, Emiliania, Eremosphaera, Ernodesmius, Euglena, Franceia, Fragilaria, Gloeothamnion, Haematococcus, Halocafeteria, Hymenomonas, Isochrysis, Lepocinclis, Micractinium, Monoraphidium, Nannochloris, Nannochloropsis, Navicula, Neochloris, Nephrochloris, Nephroselmis, Nitzschia, Ochromonas, Oedogonium, Oocystis, Ostreococcus, Pavlova, Parachlorella, Pascheria, Phaeodactylum, Phagus, Pichochlorum, Pseudoneochloris, Pseudostaurastrum, Platymonas, Pleurochrysis, Pleurococcus, Prototheca, Pseudochlorella, Pyramimonas, Pyrobotrys, Scenedesmus, Schizochlamydella, Skeletonema, Spyrogyra, Stichococcus, Tetrachlorella, Tetraselmis, Thalassiosira, Tribonema, Vaucheria, Viridiella*, and *Volvox* species, and/or one or more cyanobacteria of the *Agmenellum, Anabaena, Anabaenopsis, Anacystis, Aphanizomenon, Arthrospira, Asterocapsa, Borzia, Calothrix, Chamaesiphon, Chlorogloeopsis, Chroococcidiopsis, Chroococcus, Crinalium, Cyanobacterium, Cyanobium, Cyanocystis, Cyanospira, Cyanothece, Cylindrospermopsis, Cylindrospermum, Dactylococcopsis, Dermocarpella, Fischerella, Fremyella, Geitleria, Geitlerinema, Gloeobacter, Gloeocapsa, Gloeothece, Halospirulina, Iyengariella, Leptolyngbya, Limnothrix, Lyngbya, Microcoleus, Microcystis, Myxosarcina, Nodularia, Nostoc, Nostochopsis, Oscillatoria, Phormidium, Planktothrix, Pleurocapsa, Prochlorococcus, Prochloron, Prochlorothrix, Pseudanabaena, Rivularia, Schizothrix, Scytonema, Spirulina, Stanieria, Starria, Stigonema, Symploca, Synechococcus, Synechocystis, Tolypothrix, Trichodesmium, Tychonema*, and *Xenococcus* species.

The contactor 300 may comprise any device, vessel, container, system, or process capable of containing at least a portion of the algae media 302 and intermingling the high-$CO_2$ concentration gas 301 with the algae media 302 to exchange molecules such that concentration of $CO_2$ in the high-$CO_2$ concentration gas 301 is reduced. In at least one embodiment, the contactor 300 may comprise an algae photobioreactor (PBR). In other embodiments, however, the contactor 300 may receive the algae media 302 from an algae PBR, as discussed below. In some embodiments, the contactor 300 may be made of rigid or semi-rigid materials to contain the algae media 302. In other embodiments, however, the contactor 300 may be made of a flexible or non-rigid material, such as a bag or sheet material that will simply contain the algae media 302 but must be at least partially supported structurally against gravitational forces.

The high-$CO_2$ concentration gas 301 may be conveyed (e.g., pumped) to the contactor 300 via a gas line 304. In some embodiments, as illustrated, the gas line 304 may be fluidly coupled to a gas manifold 306 and one or more nozzles 308 may extend from the gas manifold 306 and into the interior of the contactor 300 to discharge (e.g., inject) the high-$CO_2$ concentration gas 301 into the algae media 302. This process is often referred to as "sparging". As the high-$CO_2$ concentration gas 301 contacts the algae media 302, the $CO_2$ present in the high-$CO_2$ concentration gas 301 is consumed by the algae media 302 and a vapor phase 310 of the gas 301 having a reduced concentration of $CO_2$ collects near the top of the collector 300. A gas 312 having a reduced concentration of $CO_2$ may then be discharged (drawn) out of the collector 300 via a gas discharge line 314 and conveyed downstream to be dehydrated, for example.

In some embodiments, as briefly mentioned above, the algae media 302 may be circulated (e.g., pumped, conveyed, etc.) into the contactor 300 from an adjacent algae photobioreactor (PBR) 316 and returned to the PBR 316 after interaction (contacting) with the high-$CO_2$ concentration gas 301. In such embodiments, the PBR 316 may comprise, for example, a tubular-type enclosed reactor and the algae media 302 may be extracted (drawn) from the PBR 316 in full or in part. For example, in such embodiments, a first or "inlet" conduit 318a may extend between the PBR 316 and the contactor 300, and all or a portion of the algae media 302 within the PBR 316 may be continuously or intermittently drawn from the PBR 316 and into the contactor 300 via the inlet conduit 318a. After contacting the high-$CO_2$ concentration gas 301 sparged into the contactor 300, the algae media 302 may be recycled back to the PBR 316 via a second or "outlet" conduit 318b.

While not shown, the gas line 304, the gas manifold 306, the gas discharge line 314, and the inlet and outlet conduits 318a,b may include one or more valves used to control the influx and extraction of fluids (liquids and gases) throughout the contactor 300. For example, one or more valves may be included in the gas line 304 and/or the gas manifold 306 to control the timing and amount of the high-$CO_2$ concentration gas 301 introduced (sparged) into the contactor 300. One or more additional valves may be included in the gas discharge line 314 to control the timing and amount of the gas 312 with reduced $CO_2$ concentration of extracted from the contactor 300. Moreover, one or more additional valves may be included in the inlet and outlet conduits 318a,b to control the timing and amount of the algae media 302 introduced into and extracted from the contactor 300. Some or all of these valves may be manually operable. However, operation of the some or all of the valves may alternatively be automated based on sensed operational parameters of the collector 300. In such embodiments, the collector 300 may include an automated system (e.g., a computer system) that monitors flow rates and total volumes within the collector 300 and may be programmed to actuate valves, pumps, and associated components to adjust flows, control algae growth, and maintain proper fluid levels.

In some embodiments, as briefly mentioned above, the contactor 300 may comprise a photobioreactor and otherwise operate as the PBR 316. In such embodiments, the walls of the contactor 300 may be at least partially made of any transparent or translucent material that permits the penetration (propagation) of light therethrough to provide photonic energy input for the algae media 302 contained therein. In such embodiments, suitable materials for the contactor 300 include, but are not limited to, glass, a polymer (e.g., polycarbonate, etc.), acrylic, a composite material (e.g., fiberglass), or any combination thereof. Moreover, in such embodiments, the inlet conduit 318*a* may be used to introduce nutrients and algae strains into the contactor 300 for algae growth, and the outlet conduit 318*b* may be used to dilute the algae media 302 and otherwise harvest the algae for biofuel production. In embodiments where the contactor 300 does not operate as the PBR 316, suitable materials for the contactor 300 can include any of the foregoing, but may also include a metal or concrete to cover large ranges of pressure.

In some embodiments, the contactor 300 may comprise a pressure vessel and may otherwise be capable of being pressurized to a pressure consistent with the elevated pressure of the incoming stream of high-$CO_2$ concentration gas 301. This may be especially advantageous when the high-$CO_2$ concentration gas 301 comprises a natural gas reserve, which is commonly conveyed at elevated pressures within pipelines. In such embodiments, the fluid pressure within the contactor 300 may range between about 500 psig and about 2000 psig, and the algae media 302 may be pumped into the contactor 300 at a pressure proportional to the internal pressure of the contactor 300. The rate of flow of the high-$CO_2$ concentration gas 301 through the contactor 300 may be proportional to the $CO_2$ consumption by the algae in the algae media 302 (e.g., pH-control). As a result, the high pressure of the high-$CO_2$ concentration gas 301 (e.g., natural gas) may be maintained at elevated pipeline pressures for end users.

In some embodiments, the contactor 300 may be located near a power plant where the gas 312 with reduced $CO_2$ concentration may be combusted to make electrical power. Moreover, the flue gas generated by the power plant will have a high concentration of $CO_2$, which could then be recirculated through the contactor 300 (e.g., via the gas line 304 and the gas manifold 306) to feed the algae media 302. In some embodiments, the contactor 300 may include a plurality of contactors used in parallel or series to facilitate multistage contacting. As will be appreciated, this may optimize the process depending on variables such as the concentration of the high-$CO_2$ concentration gas 301, the pressure within the contactor(s) 300, etc.

The byproduct generated through photosynthesis of the algae media 302 is oxygen ($O_2$). This byproduct is significant since $O_2$ is a necessary reaction product in many industries, such as oxycombustion power, hydrogen generation, and syngas generation (collectively referred to herein as "oxygen-requiring processes"). According to one or more embodiments of the present disclosure, a stream of natural gas or biogas may be enriched with $O_2$ by circulating the natural gas or biogas through a photobioreactor (PBR) used for algae growth. As it interacts with the algae media 302 contained within the PBR, the natural gas or biogas strips off (harvests) the $O_2$ from the algae media 302 and the PBR discharges a combustible gas enriched with $O_2$. Moreover, if the natural gas or biogas entering the PBR has a high $CO_2$ content, the algae media 302 will consume the $CO_2$, thus simultaneously reducing the $CO_2$ content of the natural gas or biogas as it intermingles with the algae media 302.

Figure 4:
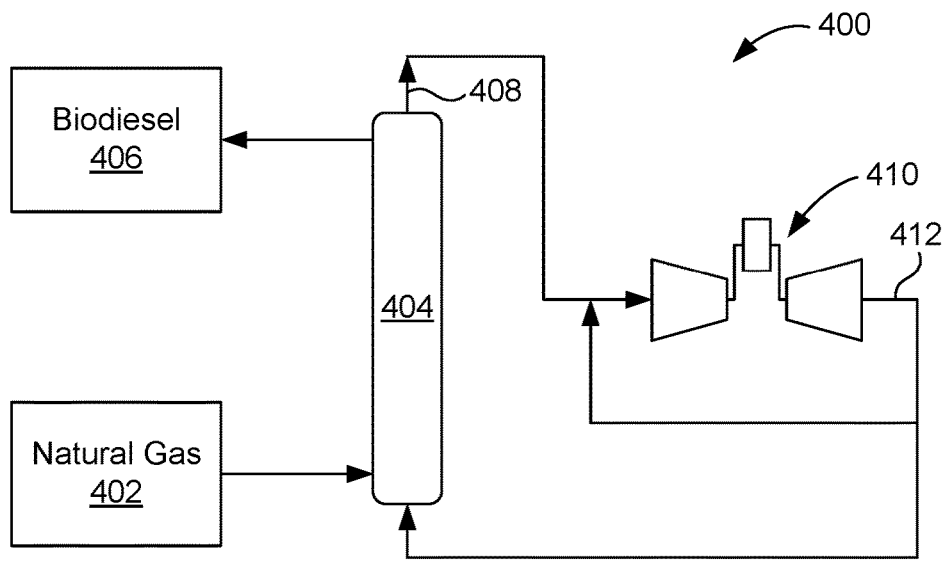
FIG. 4 is an example system for enriching a stream of natural gas with oxygen, according to one or more embodiments.

FIG. 4 is an example system 400 for enriching a stream of natural gas 402 with oxygen ($O_2$), according to one or more embodiments. In at least one embodiment, the natural gas 402 may be replaced with a biogas generated through anaerobic digestion, and the system 400 may alternatively be configured to enrich a stream of biogas with $O_2$, without departing from the scope of the disclosure.

The natural gas 402 may be the same as or similar to the natural gas 102 described above. Accordingly, the natural gas 402 may comprise any natural gas stream or reserve and, in at least one embodiment, the natural gas 402 may comprise up to about 80 wt % $CO_2$, but could be as low was 10 wt % or 5 wt %. The natural gas 402 may be introduced into a photobioreactor (PBR) 404 used for algae growth and for the production of biodiesel 406. In some embodiments, the PBR 404 may be the same as the contactor 300 of FIG. 3. As the natural gas 402 contacts the algae media contained within the PBR 404, the algae media consumes $CO_2$ contained in the natural gas 402 and generates $O_2$ as a byproduct. In the process, the natural gas 402 strips (harvests) the $O_2$ from the algae media and the PBR 404 discharges an $O_2$-enriched natural gas 408 that can be used in a downstream oxygen-requiring process. As will be appreciated, this may help regulate the amount of $O_2$ in the PBR 404, thus helping to maintain a healthy environment for the algae media contained therein.

In some embodiments, the $O_2$-enriched natural gas 408 may be used in an oxycombustion process, which involves burning a fuel (e.g., natural gas) using $O_2$ instead of air as the primary oxidant to produce power. As illustrated, for example, the $O_2$-enriched natural gas 408 may be conveyed to a combustion power plant 410 where the $O_2$-enriched natural gas 408 is combusted to generate heat for power production. Since the fuel is already enriched with $O_2$, the $O_2$-enriched natural gas 408 can be directly combusted in the combustion power plant 410 without the addition of $O_2$. The byproducts 412 generated by the combustion power plant 410, such as $CO_2$, water, and nitrogen oxides (NOx), can be fed back to the PBR 404 to be used as feedstock for the algae media contained therein. The algae consume $CO_2$, but can also consume NOx since the algae consume nitrogen as nitrate, which satisfies some of the nutrition requirements of the algae while allowing for higher flame temperatures in the combustion power plant 410. Although higher flame temperatures generally imply higher cycle efficiencies in power generation, such temperatures often generate more NOx, which can be problematic for the combustion system.

Figure 5:
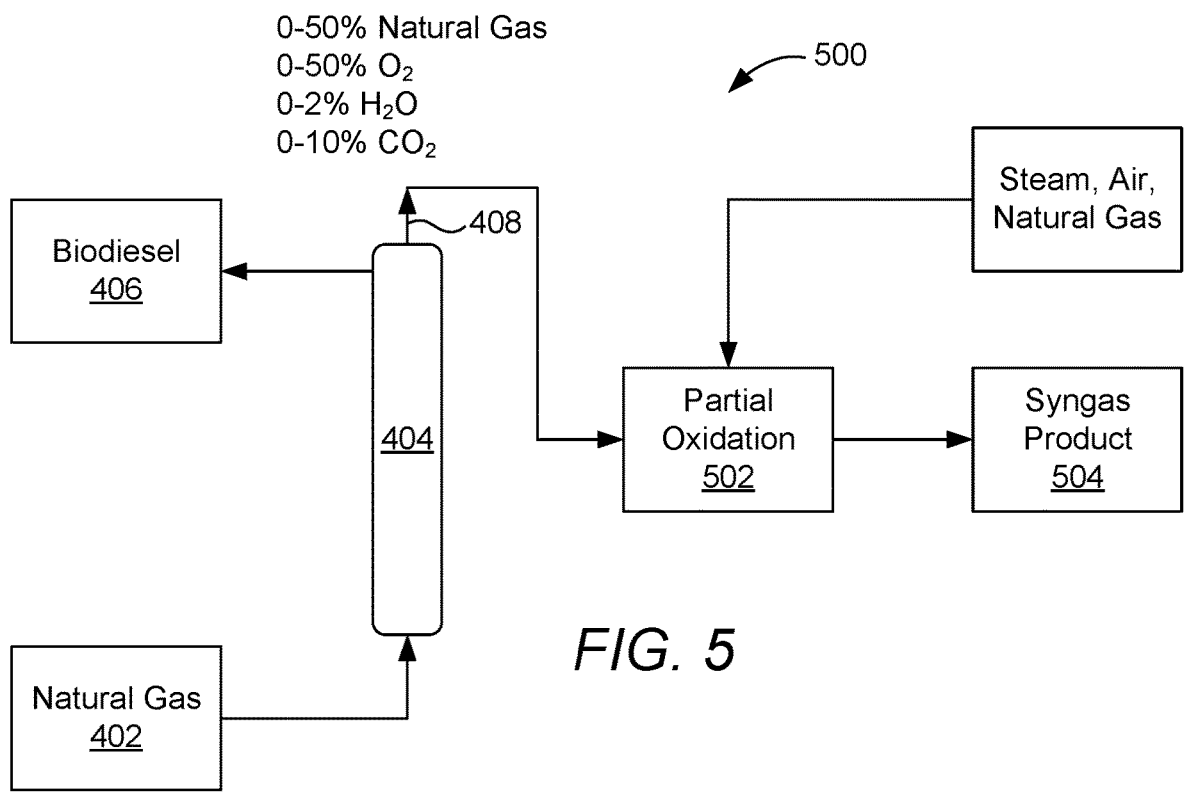
FIG. 5 is another example system for enriching the stream of natural gas with oxygen, according to one or more additional embodiments.

FIG. 5 is another example system 500 for enriching the stream of natural gas 402 with oxygen ($O_2$), according to one or more additional embodiments. As with the system 500, the natural gas 402 may be replaced with a biogas and the system 500 may alternatively be configured to enrich a stream of biogas with $O_2$, without departing from the scope of the disclosure. The system 500 may be similar in some respects to the system 400 of FIG. 4 and thus may be best understood with reference thereto, where like numerals will represent like components not described again in detail. As illustrated, for example, the system 500 includes the natural gas 402 being introduced into the PBR 404 for algae growth and for the production of the biodiesel 406. Moreover, the PBR 404 discharges the $O_2$-enriched natural gas 408, which may include 0-50 wt % natural gas, 0-50 wt % $O_2$, 0-2 wt % $H_2O$, and 0-10 wt % $CO_2$.

Unlike the system 400 of FIG. 4, however, the system 500 may be configured to feed the $O_2$-enriched natural gas 408 to a synthesis gas ("syngas") production process for the manufacture (production) of various products, such as gas, diesel, and chemicals. More specifically, the $O_2$-enriched natural gas 408 may be fed to a partial oxidation system 502 for syngas production. Syngas can be produced from many sources, including natural gas, biogas, coal, or virtually any hydrocarbon feedstock, by reaction with steam (i.e., steam reforming), $CO_2$ (i.e., dry reforming), or oxygen (i.e., partial oxidation). Pure oxygen is required in such a process to reduce the amount of nitrogen in the syngas product, and nitrogen is an inert diluent that greatly increases the cost of downstream processing when converting the syngas to the various use products.

In the illustrated embodiment, the $O_2$-enriched natural gas 408 may be fed into the partial oxidation syngas production 502 facility to produce a syngas product 504. In some embodiments, supplemental gases, such as steam, air, and natural gas, may be added to the partial oxidation syngas production 502 as needed. Moreover, any byproducts from the partial oxidation 502 syngas process, including carbon monoxide and hydrogen, can be used to synthesize fuels downstream of the syngas unit.

EMBODIMENTS LISTING

The present disclosure provides, among others, the following embodiments, each of which may be considered as optionally including any alternate embodiments.

Clause 1. A method, comprising: containing an algae media within a contactor; introducing a stream of natural gas comprising up to 80 wt % carbon dioxide ($CO_2$) into the contactor; contacting the natural gas on the algae media and thereby allowing the algae media to consume $CO_2$ from the natural gas; and discharging a stream of natural gas comprising 2 wt % or less $CO_2$ from the contactor.

Clause 2. The method of clause 1, wherein the contactor comprises an algae photobioreactor.

Clause 3. The method of clause 1 or clause 2, wherein containing the algae media within the contactor comprises circulating the algae media into the contactor from an algae photobioreactor; and returning the algae media to the algae photobioreactor after contacting the natural gas on the algae media within the contactor.

Clause 4. The method of clause 3, wherein the algae photobioreactor comprises an enclosed reactor.

Clause 5. The method of any of the preceding Clauses, further comprising conveying the stream of natural gas discharged from the contactor to a power plant for combustion.

Clause 6. The method of any of the preceding Clauses, further comprising: pressurizing the contactor to a fluid pressure between about 500 psig and about 2000 psig; and discharging the stream of natural gas from the contactor into a pressurized pipeline.

Clause 7. The method of any of the preceding Clauses, further comprising: generating oxygen ($O_2$) with the algae media; stripping at least a portion of the $O_2$ with the natural gas within the contactor and thereby discharging a stream of natural gas enriched with $O_2$ from the contactor; and using the stream of natural gas enriched with $O_2$ in an oxygen-requiring process.

Clause 8. The method of Clause 7, wherein the oxygen-requiring process comprises at least one of syngas production and oxycombustion for power production.

Clause 9. A method, comprising introducing a stream of natural gas into an algae photobioreactor (PBR) containing an algae media; generating oxygen (O2) with the algae media; stripping at least a portion of the O2 with the natural gas within the PBR; and discharging a stream of natural gas enriched with O2 from the PBR; and using the stream of natural gas enriched with O2 in an oxygen-requiring process.

Clause 10. The method of Clause 9, wherein the natural gas comprises up to 80 wt % carbon dioxide ($CO_2$), and wherein generating the $O_2$ with the algae media comprises: contacting the natural gas on the algae media; and consuming at least a portion of the $CO_2$ from the natural gas with the algae media.

Clause 11. The method of Clause 9 or Clause 10, wherein using the stream of natural gas enriched with O2 in an oxygen-requiring process comprises: conveying the stream of natural gas enriched with $O_2$ to a combustion power plant; and combusting the stream of natural gas enriched with $O_2$ in the combustion power plant to generate power.

Clause 12. The method of Clause 9 or Clause 10, wherein using the stream of natural gas enriched with O2 in an oxygen-requiring process comprises: conveying the stream of natural gas enriched with $O_2$ to a partial oxidation system; and generating a syngas product in the partial oxidation system with the stream of natural gas enriched with $O_2$.

Clause 13. The method of any of claims 9 to 12, wherein the algae photobioreactor comprises an enclosed reactor.

Clause 14. The method of any of claims 9 to 13, wherein using the stream of natural gas enriched with $O_2$ in an oxygen-requiring process is preceded by dehydrating the stream of natural gas enriched with $O_2$.

Clause 15. A method, comprising: introducing a stream of a high-carbon dioxide ($CO_2$) concentration gas into a contactor containing an algae media, the high-$CO_2$ concentration gas comprising at one of natural gas having up to 80 wt % $CO_2$ and a biogas having about 20-40 wt % $CO_2$; contacting the high-$CO_2$ concentration gas on the algae media and thereby allowing the algae media to consume $CO_2$ from the high-$CO_2$ concentration gas; and discharging a stream of gas comprising 2 wt % or less $CO_2$ from the contactor.

Clause 16. The method of Clause 15, wherein the contactor comprises an algae photobioreactor.

Clause 17. The method of Clause 15 or Clause 16, wherein containing the algae media within the contactor comprises: circulating the algae media into the contactor from an algae photobioreactor; and returning the algae media to the algae photobioreactor after contacting the natural gas on the algae media within the contactor.

Clause 18. The method of any of Clauses 15-17, further comprising conveying the stream of gas discharged from the contactor to a power plant for combustion.

Clause 19. The method of any of Clauses 15-18, further comprising: pressurizing the contactor to a fluid pressure between about 500 psig and about 2000 psig; and discharging the stream of gas from the contactor into a pressurized pipeline.

Clause 20. The method of any of Clauses 15-19, further comprising: generating oxygen ($O_2$) with the algae media; stripping at least a portion of the $O_2$ with the high-$CO_2$ concentration gas within the contactor and thereby discharging a stream of gas enriched with $O_2$ from the contactor; and using the stream of gas enriched with $O_2$ in an oxygen-requiring process.

Therefore, the disclosed systems and methods are well adapted to attain the ends and advantages mentioned as well as those that are inherent therein. The particular embodiments disclosed above are illustrative only, as the teachings of the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope of the present disclosure. The systems and methods illustratively disclosed herein may suitably be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the elements that it introduces. If there is any conflict in the usages of a word or term in this specification and one or more patent or other documents that may be incorporated herein by reference, the definitions that are consistent with this specification should be adopted.

As used herein, the phrase "at least one of" preceding a series of items, with the terms "and" or "or" to separate any of the items, modifies the list as a whole, rather than each member of the list (i.e., each item). The phrase "at least one of" allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

The invention claimed is:

1. A method, comprising:
containing an algae media within a contactor;
introducing a stream of natural gas comprising up to 80 wt % carbon dioxide ($CO_2$) and having a fluid pressure in a range of 500 psig to 2000 psig into the contactor;
maintaining the fluid pressure within the contactor in the range;
contacting the natural gas on the algae media and thereby allowing the algae media to consume $CO_2$ from the natural gas; and
discharging a stream of natural gas comprising 2 wt % or less $CO_2$ from the contactor at a fluid pressure in the range into a pressurized pipeline.

2. The method of claim 1, wherein the contactor comprises an algae photobioreactor.

3. The method of claim 1, wherein containing the algae media within the contactor comprises:
circulating the algae media into the contactor from an algae photobioreactor; and
returning the algae media to the algae photobioreactor after contacting the natural gas on the algae media within the contactor.

4. The method of claim 3, wherein the algae photobioreactor comprises an enclosed reactor.

5. The method of claim 1, further comprising conveying the stream of natural gas discharged from the contactor to a power plant for combustion.

6. The method of claim 1, further comprising:
generating oxygen ($O_2$) with the algae media;
stripping at least a portion of the $O_2$ with the natural gas within the contactor and thereby discharging a stream of natural gas enriched with $O_2$ from the contactor; and
using the stream of natural gas enriched with $O_2$ in an oxygen-requiring process.

7. The method of claim 6, wherein the oxygen-requiring process comprises at least one of syngas production and oxycombustion for power production.

8. A method, comprising:
introducing a stream of natural gas having a fluid pressure in a range of 500 psig to 2000 psig into an algae photobioreactor (PBR) containing an algae media;
generating oxygen ($O_2$) with the algae media;
stripping at least a portion of the $O_2$ with the natural gas within the PBR;
discharging a stream of natural gas enriched with $O_2$ from the PBR at the fluid pressure in the range; and
using the stream of natural gas enriched with $O_2$ in an oxygen-requiring process.

9. The method of claim 8, wherein the natural gas comprises up to 80 wt % carbon dioxide ($CO_2$), and wherein generating the $O_2$ with the algae media comprises:
contacting the natural gas on the algae media; and
consuming at least a portion of the $CO_2$ from the natural gas with the algae media.

10. The method of claim 8, wherein using the stream of natural gas enriched with $O_2$ in an oxygen-requiring process comprises:
conveying the stream of natural gas enriched with $O_2$ to a combustion power plant; and
combusting the stream of natural gas enriched with $O_2$ in the combustion power plant to generate power.

11. The method of claim 8, wherein using the stream of natural gas enriched with $O_2$ in an oxygen-requiring process comprises:
conveying the stream of natural gas enriched with $O_2$ to a partial oxidation system; and
generating a syngas product in the partial oxidation system with the stream of natural gas enriched with $O_2$.

12. The method of claim 8, wherein the algae photobioreactor comprises an enclosed reactor.

13. The method of claim 8, wherein using the stream of natural gas enriched with $O_2$ in an oxygen-requiring process is preceded by dehydrating the stream of natural gas enriched with $O_2$.

14. A method, comprising:
introducing a stream of a high-carbon dioxide ($CO_2$) concentration gas with a fluid pressure in a range of 500 psig to 2000 psig into a contactor containing an algae media, wherein the high-$CO_2$ concentration gas comprising at a natural gas having up to 80 wt % $CO_2$;
contacting the high-$CO_2$ concentration gas on the algae media and thereby allowing the algae media to consume $CO_2$ from the high-$CO_2$ concentration gas; and
discharging a stream of gas comprising 2 wt % or less $CO_2$ from the contactor at the fluid pressure in a range of 500 psig to 2000 psig into a pressurized pipeline.

15. The method of claim 14, wherein the contactor comprises an algae photobioreactor.

16. The method of claim 14, wherein containing the algae media within the contactor comprises:

circulating the algae media into the contactor from an algae photobioreactor; and returning the algae media to the algae photobioreactor after contacting the natural gas on the algae media within the contactor.

17. The method of claim 14, further comprising conveying the stream of gas discharged from the contactor to a power plant for combustion.

18. The method of claim 14, further comprising:

generating oxygen ($O_2$) with the algae media;

stripping at least a portion of the $O_2$ with the high-$CO_2$ concentration gas within the contactor and thereby discharging a stream of gas enriched with $O_2$ from the contactor; and using the stream of gas enriched with $O_2$ in an oxygen-requiring process.

* * * * *